United States Patent
Lamba et al.

(10) Patent No.: US 12,324,595 B2
(45) Date of Patent: Jun. 10, 2025

(54) ADJUSTABLE REAMER DRIVER AND IMPACTOR, AND METHODS OF PREPARING SAID DRIVER AND IMPACTOR

(71) Applicant: DEPUY IRELAND UNLIMITED COMPANY, Ringaskiddy (IE)

(72) Inventors: Arjun Lamba, Ringaskiddy (GB); Sandesh Hemmuru Devaraja, Karnataka (IN); Vivek Thunoli, Leeds (GB); Duncan Beedall, Leeds (GB); James Naylor, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 388 days.

(21) Appl. No.: 17/781,153

(22) PCT Filed: Dec. 1, 2020

(86) PCT No.: PCT/EP2020/084162
§ 371 (c)(1),
(2) Date: May 31, 2022

(87) PCT Pub. No.: WO2021/110699
PCT Pub. Date: Jun. 10, 2021

(65) Prior Publication Data
US 2023/0000500 A1  Jan. 5, 2023

(30) Foreign Application Priority Data
Dec. 2, 2019  (IN) .............................. 201911049507

(51) Int. Cl.
*A61B 17/16* (2006.01)
*A61B 17/92* (2006.01)
*A61B 17/00* (2006.01)

(52) U.S. Cl.
CPC .......... *A61B 17/1666* (2013.01); *A61B 17/92* (2013.01); *A61B 2017/00464* (2013.01);
(Continued)

(58) Field of Classification Search
CPC ............ A61B 17/1662; A61B 17/1664; A61B 17/1666; A61B 17/92
See application file for complete search history.

(56) References Cited

U.S. PATENT DOCUMENTS 7,601,155 B2  10/2009  Petersen
8,753,346 B2   4/2014  Bergin
(Continued)

FOREIGN PATENT DOCUMENTS

CN  101883540 A  11/2010
CN  102665591 A   9/2012
(Continued)

OTHER PUBLICATIONS

International Search Report From Ep Application No. EP2018/071060, Dated Nov. 13, 2018, 3 Pages.
(Continued)

*Primary Examiner* — Si Ming Ku
(74) *Attorney, Agent, or Firm* — Barnes & Thornburg LLP

(57) ABSTRACT

An instrument comprising a body comprising a distal end spaced apart from a proximal end relative to a longitudinal axis and a handle coupling located near the proximal end, the body defining a channel miming between the distal end to the proximal end; a drive comprising a first connector located adjacent the distal end and adapted to be connected to a driven instrument, a second connector located adjacent the proximal end and adapted to be connected to a driving instrument, and a drive shaft arranged in the channel, the drive shaft coupling the second connector to the first con- (Continued)

nector; and an adjustable handle located near the distal end, the adjustable handle comprising a grip spacing apart a leading end from a trailing end along a handle axis, the leading end coupling the handle to the handle coupling, the trailing end shaped to define an impaction plate; wherein the adjustable handle is arrangeable relative to the body in a first and a second position, in the first position the leading end is arranged relative to the handle coupling such that the handle axis is offset relative to the longitudinal axis, and in the second position the leading end is arranged relative to the handle coupling such that the handle axis is parallel to the longitudinal axis.

9 Claims, 8 Drawing Sheets

(52) U.S. Cl.
CPC .............. *A61B 2017/00469* (2013.01); *A61B 2017/924* (2013.01)

(56) References Cited

U.S. PATENT DOCUMENTS

| | | |
|---|---|---|
| 8,690,875 B2 | 6/2014 | Soares |
| 9,447,803 B1 | 9/2016 | Fu |
| 9,458,890 B1 | 10/2016 | Fu |
| 9,877,763 B2 | 1/2018 | Barth |
| 10,265,084 B2 | 4/2019 | Ujvari |
| 11,540,840 B2 | 1/2023 | Cannon et al. |
| 2003/0023256 A1 | 1/2003 | Estes |
| 2003/0090698 A1 | 5/2003 | Maes et al. |
| 2003/0163134 A1 | 8/2003 | Riedel |
| 2006/0053974 A1 | 3/2006 | Blust |
| 2007/0293869 A1 | 12/2007 | Conte et al. |
| 2008/0275450 A1 | 11/2008 | Myers et al. |
| 2010/0063524 A1 | 3/2010 | McCombs |
| 2011/0082462 A1 | 4/2011 | Suarez |
| 2012/0253323 A1 | 10/2012 | Bharadwaj |
| 2014/0207141 A1 | 7/2014 | Kehres |
| 2014/0243831 A1 | 8/2014 | Witt |
| 2015/0238242 A1 | 8/2015 | Barth et al. |
| 2016/0051266 A1 | 2/2016 | Krebs |
| 2016/0175112 A1* | 6/2016 | Pruvost .............. A61B 17/1633 606/81 |
| 2017/0027594 A1 | 2/2017 | Ujvari |
| 2021/0128174 A1 | 5/2021 | Cannon |
| 2023/0000500 A1 | 1/2023 | Lamba et al. |

FOREIGN PATENT DOCUMENTS

| | | |
|---|---|---|
| EP | 2272446 A2 | 1/2011 |
| JP | 2015527150 B2 | 9/2015 |
| WO | 2009046121 A2 | 4/2009 |

OTHER PUBLICATIONS

Japanese Search Report From Japanese Application No. JP2020-511275, Dated May 24, 2022, 8 Pages.

Chinese Search Report From Chinese Application No. 201880054518, Dated Dec. 22, 2022, 2 Pages.

PCT/EP2020/084162—International Search Report Dated Jun. 15, 2021.

* cited by examiner

ADJUSTABLE REAMER DRIVER AND IMPACTOR, AND METHODS OF PREPARING SAID DRIVER AND IMPACTOR

CROSS-REFERENCE TO RELATED APPLICATIONS

This application is a National Stage Application filed Under 35 U.S.C. § 371of International Application No. PCT/EP2020/084162 filed Dec. 1, 2020, which claims priority to Indian application Ser. No. 201911049507 filed Dec. 2, 2019, which are hereby incorporated by reference in their entireties.

The present invention relates to adjustable reamer drivers and impactors, methods of preparing said driver and impactor for use, and methods of reaming and impacting using said reamer drivers and impactors.

BACKGROUND TO THE INVENTION

Human and animal bodies have various joints, such as ankles, knees, hips, shoulders and elbows. The joints are formed where two or more skeletal bones meet. Many joints permit movement between those two or more bones.

Between the joints of a body that permit motion, typically, cartilage is found. Cartilage provides lubrication for the motion and absorbs some of the forces to which a joint is subjected.

The cartilage may wear down over time. As a consequence, the bones making up a joint may come into contact leading to pain and reduced joint function. Other causes of joint damage is arthropathy. Arthropathy, such as arthritis, is a disease of the joint that may lead to conditions such as pain, stiffness and swelling.

An option to treat damaged joints is to replace the parts of the joint that are degraded or diseased with a prosthesis. A commonly used prosthesis is a total joint prosthesis. The total joint prosthesis is used to replace native or natural joint parts with an artificial joint. For example, in a total hip replacement procedure, a natural hip joint may be treated with a total hip replacement prosthesis. The total hip replacement prosthesis includes an artificial femoral part and an artificial acetabular part.

During a surgical procedure to replace a joint, the joint is prepared to receive its respective part using specialized instrumentation. One such instrument is a reamer. Reamers are an instrument used to remove parts of a bone to be replaced and may be used to shape the bone to receive the appropriate prosthetic member.

In a total hip replacement, reamers and impactors may be used to prepare the acetabulum of a recipient to receive a replacement cup prosthesis. Acetabular reamers are typically hemispherical and are used prepare a correspondingly shaped cavity in the acetabulum. Impactors are typically used to impact various parts used in other parts of the procedure.

A known modular acetabular impactor and reamer system is disclosed by a US patent application with patent publication number US 2016/175,112. The modular acetabular impactor and reamer system includes a main body extending between a proximal handle end and a distal end. The system also includes a transmission rotatingly extending within the main body. The transmission has an accessory mount. The system also has at least one impactor handle and a reamer handle removably coupled to the main body proximal handle end. The impactor handle has a drive shaft to drive rotation relative to the impactor handle. The reamer handle has a drive mount to drive rotation relative to the reamer handle. The system also has at least one impactor cup and a reamer module removably coupled to the main body distal end. The transmission and the at least one impactor cup and the reamer module correspondingly rotate relative to the main body.

This known modular acetabular impactor and reamer system features multiple components and may be complicated to configure or switch between the different modes of operation.

SUMMARY OF THE INVENTION

According to a first aspect of the present invention, an instrument configurable as a reamer and an impactor. The instrument has a body, a drive and an adjustable handle. The body has a distal end spaced apart from a proximal end relative to a longitudinal axis. The body has a handle coupling located near the proximal end. The body defines a channel running between the distal end to the proximal end. The drive has a first connector, a second connector and a drive shaft. The first connector is located adjacent the distal end of the body. The first connector is adapted to be connected to a driven instrument, such as, for example, a reamer head. The second connector is located adjacent the proximal end of the body. The second connector is adapted to be connected to a driving instrument, such as, for example, a power tool. The drive shaft is arranged in the channel. The drive shaft couples the second connector to the first connector. The adjustable handle is located near the distal end of the body. The adjustable handle comprises a grip spacing apart a leading end from a trailing end along a handle axis. The leading end couples the handle to the handle coupling. The trailing end is shaped to define an impaction plate. The adjustable handle is arrangeable relative to the body in a first and a second position. In the first position the leading end is arranged relative to the handle coupling such that the handle axis is offset relative to the longitudinal axis. In the second position the leading end is arranged relative to the handle coupling such that the handle axis is parallel to the longitudinal axis.

A benefit of the instrument of the present invention is that the same handle can be used for different procedures. The provision of a single handle that enables the instrument to be adapted for at least a first and a second function may result in a less complicated process for configuring the instrument for different purposes. For example, the handle enables the instrument, in one configuration, to be adapted for use as a reamer and, in another configuration, to be adapted for use as an impactor. Such a handle may be easier to configure and improve efficiency with respect to known handles.

Preferably, in the second position, the impaction plate is perpendicular to the longitudinal axis.

Preferably, in the first position, the second connecter is engageable by the driving instrument, and the adjustable handle can be gripped by a user to provide additional support.

Preferably, the adjustable handle is rotatably coupled to the handle coupling distal end of the body.

Preferably, the adjustable handle is coupled to the handle coupling by a joint, the joint configured to enable adjustable handle to be swiveled between the first and second positions.

Preferably, the adjustable handle is removable from the handle coupling to enable arrangement of the adjustable handle in one of the first or second positions.

Preferably, the handle coupling has a faceted recess and the leading end of the adjustable handle is faceted. The leading end of the adjustable handle may be removable from the faceted recess and, due to the facets, may be capable of being selectively arranged into the faceted recess in either the first or the second position.

Preferably, when viewed in cross section, the faceted recess and the faceted leading end have the same polygonal shape.

Preferably, the instrument has a holding mechanism to hold the handle in the first and second positions. Preferably, the holding mechanism includes a latch to retain the handle in one of the first or second positions and a release mechanism to unlatch the latch so that the handle can be moved between the first and second positions.

According to a second aspect of the present invention, there is provided an instrument having a body, a drive mechanism and an actuator. The body has a proximal end and a distal end. The body defines a channel running from an opening in the proximal end to an opening in the distal end. The drive mechanism has a first coupling located near the proximal end connected by a drive shaft located in the channel to a second coupling located near the distal end. The draft shaft arranged to transmit torque applied to one of the couplings to the other. The actuator is arrangeable between a first and a second position relative to the first coupling. In the first position the actuator is engaged with the first coupling and is manipulatable to transmit an applied torque to the first coupling. In the second position the actuator is disengaged from the first coupling and is unable to transmit a torque to the first coupling.

According to a third aspect of the present invention, there is provided a method of preparing an instrument. The method includes the steps of:
  providing an instrument comprising:
    a body comprising a distal end spaced apart from a proximal end relative to a longitudinal axis and a handle coupling located near the proximal end, the body defining a channel running between the distal end to the proximal end,
    a drive comprising a first connector located adjacent the distal end and adapted to be connected to a driven instrument, a second connector located adjacent the proximal end and adapted to be connected to a driving instrument, and a drive shaft arranged in the channel, the drive shaft coupling the second connector to the first connector, and
    an adjustable handle located near the distal end, the adjustable handle comprising a grip spacing apart a leading end from a trailing end along a handle axis, the leading end coupling the handle to the handle coupling, the trailing end shaped to define an impaction plate; and
    arranging the adjustable handle to be in one of a first or a second position.

In the first position the adjustable handle may be arranged such that the leading end is arranged relative to the handle coupling such that the handle axis is offset relative to the longitudinal axis.

In the second position the adjustable handle may be arranged such that the leading end is arranged relative to the handle coupling such that the handle axis is parallel to the longitudinal axis.

Preferably, in the second position, the impaction plate is perpendicular to the longitudinal axis.

Preferably, in the first position, an operator engages the second connecter with a driving instrument, and the adjustable handle is gripped by the operator.

Preferably, the adjustable handle is rotatably coupled to the handle coupling distal end of the body.

Preferably, the adjustable handle is coupled to the handle coupling by a joint. The joint may be configured to enable adjustable handle to be swiveled between the first and second positions.

Preferably, the adjustable handle is removable from the handle coupling to enable arrangement of the adjustable handle in one of the first or second positions.

Preferably, the handle coupling comprises a faceted recess and the leading end of the adjustable handle is faceted. The leading end of the adjustable handle may be removable from the faceted recess and, due to the facets, may be capable of being selectively arranged into the faceted recess in either the first or the second position.

Preferably, when viewed in cross section, the faceted recess and the faceted leading end have the same polygonal shape.

Preferably, the instrument includes a holding mechanism to hold the handle in the first and second positions. Preferably, the holding mechanism comprises a latch to retain the handle in one of the first or second positions. The method may include the step of pressing the latch to unlatch a release mechanism so that the handle can be moved between the first and second positions.

A BRIEF DESCRIPTION OF THE DRAWINGS

For a more complete understanding of the present invention and the advantages thereof, reference is --- made to the following description taken in connection with the following drawings, in which.

DETAILED DESCRIPTION OF THE PREFERRED EMBODIMENTS

The present invention is a surgical instrument that has multiple functions. In the first exemplary function, the instrument is used for reaming. In the second exemplary function, the instrument is used for impaction. To switch between one functional mode and the other, the instrument has an adjustable handle. The adjustable handle is rearrangeable between first and second positions. In the first position, handle is arranged to facilitate reaming. In the second position, the handle is arranged to facilitate impaction.

The adjustable handle has a grip spacing apart a leading end from a trailing end along a handle axis. The leading end has a handle coupling configured to couple the adjustable handle to the instrument relative to a longitudinal axis running from a proximal end to a distal end of the instrument. The handle coupling enables the handle to be adjusted between the plurality of functional modes. The trailing end defines an impaction plate.

The handle can be adjusted relative to the longitudinal axis of the instrument between the first and second positions. In the first position, the leading end is arranged relative to the instrument so that the handle is offset relative to the longitudinal axis of the instrument. In the second position, the leading end is arranged relative to the handle coupling such that the handle axis is parallel to the longitudinal axis.

With the handle in the first position, the instrument is arranged in a reaming configuration.

With the handle in the second position, the handle is arranged in impaction configuration. In this configuration, the impaction plate located in the trailing end is arranged to be struck with a surgical hammer by an operator.

The instrument of the present invention has a reconfigurable handle that enables the instrument to be adapted for at least a first and a second function. For example, the handle enables the instrument, in one configuration, to be adapted for use as a reamer and, in another configuration, to be adapted for use as an impactor. Such a handle may be easier to configure and improve efficiency of a surgical procedure.

Figure 1:
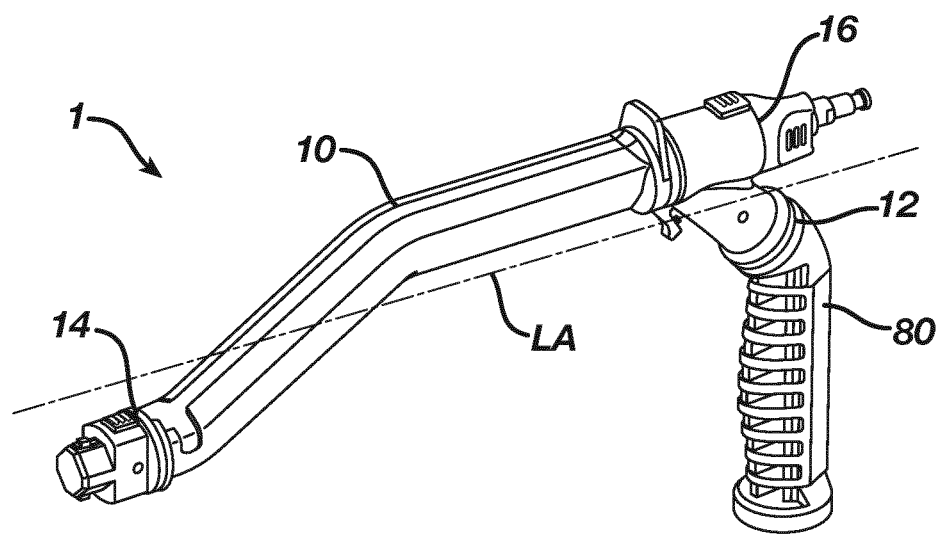
FIG. 1 shows a perspective view of the modular handle assembly of a first embodiment of the present invention.

FIG. 1 shows an instrument 1 of a first embodiment of the present invention. The instrument 1 has a body 10 and a handle 80. The handle 80 is connected to the body 10 by a handle coupling 12. The handle coupling 12 enables the handle 80 to be arrangeable in the first and second positions.

The body 10 has a distal end 14 spaced apart from a proximal end 16 relative to a longitudinal axis LA that runs relative to the body 10. The handle coupling 12 enables the handle 80 to be arranged relative to the longitudinal axis LA in the first and second positions. In the first position, the handle 80 is arranged relative to the coupling such 12 that the handle 80 is offset relative to the longitudinal axis LA. In the second position, the handle 80 is arranged relative to the handle coupling 12 such that the handle 80 is parallel to the longitudinal axis LA.

Figure 2:
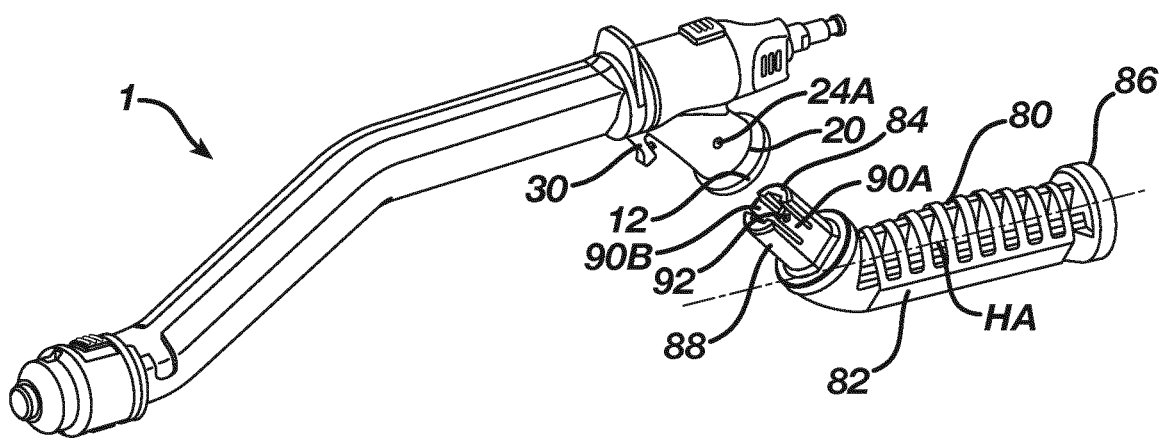
FIG. 2 shows a perspective view of the modular handle assembly of FIG. 1 set at the "Impactor" configuration showing the exploded view of proximal handle grip.

Referring to FIG. 2, the handle 80 has a grip 82 spacing apart a leading end 84 from a trailing end 86 relative to a handle axis HA.

The handle 80 is removable from the instrument 1. The handle 80 has a first coupling member 88 of the handle coupling 12. The first coupling member 88 enables the handle to be removably coupled to the instrument 1 by the handle coupling.

The first coupling member 88 is located in the vicinity of the leading end 84. The first coupling member 88 has a first and a second resilient element 90A, 90B. The resilient elements 90A, 90B each have a protrusion 92A, 92B.

Figure 3:
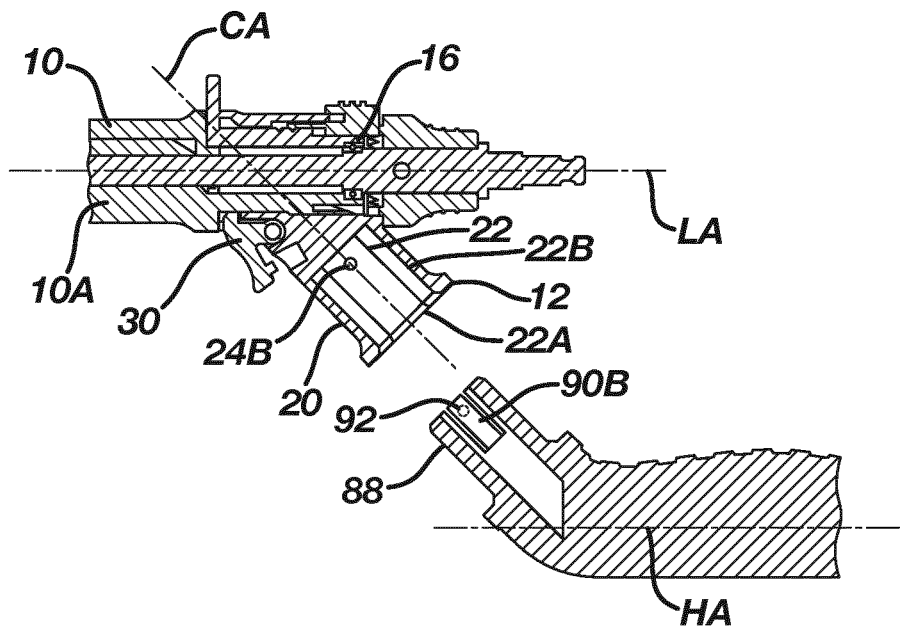
FIG. 3 shows a side view of the section of proximal end of Modular handle assembly of FIG. 1.

Referring to FIG. 3, the handle coupling 12 includes the first coupling member 88 and a second coupling member 20. The first coupling member 88 is shaped and dimensioned to be received by a second coupling member 20.

The second coupling member 20 is part of the body 10. The second coupling member 20 is located near the proximal end 16. The second coupling member 20 has a cylindrical shaped body that extends at an angle from a main portion 10A of the body 10 in a region adjacent to the proximal end 16.

The second coupling member 16 extends from the body along a coupling axis CA. The coupling axis CA is offset relative to the longitudinal axis LA. The coupling axis is offset relative to the longitudinal axis by angle of 45 degrees. Of course, as a person of skill would understand other offset angles are of course possible.

The second coupling member 20 has a cavity 22 in the body that is correspondingly shaped and dimensioned for receiving the first coupling member 88. The cavity 22 is defined by an opening 22A and a sidewall 22B. The opening 22A is located in an end of the second coupling member 20. The internal sidewalls 22B defining the cavity 22 extend along the coupling axis CA.

A press-fit is formed between the first and second coupling members 88, 20 to couple them together.

Referring to FIGS. 2 and 3, the second coupling member includes a first aperture 24A and a second aperture 24B. The apertures 24A, 24B are arranged to receive the protrusions 92A, 92B. The first aperture 24A is arranged to receive the first protrusion 92A. The second aperture 24B is arranged to receive the second protrusion 92B. When the first coupling member 88 is coupled to the second coupling member 20, the protrusions 92A, 92B are located in the apertures 24A, 24B to releasably lock the handle 80 to the body 10.

The handle coupling 12 includes a release mechanism 30. The release mechanism 30 is arranged to engage with the leading end 84 to prize the protrusions 92A, 92B out of the apertures 24A, 24B. Removal of the protrusions 92A, 92B from the apertures 24A, 24B releases the lock and enables the handle 80 to be removed from the body 10.

Figure 4:
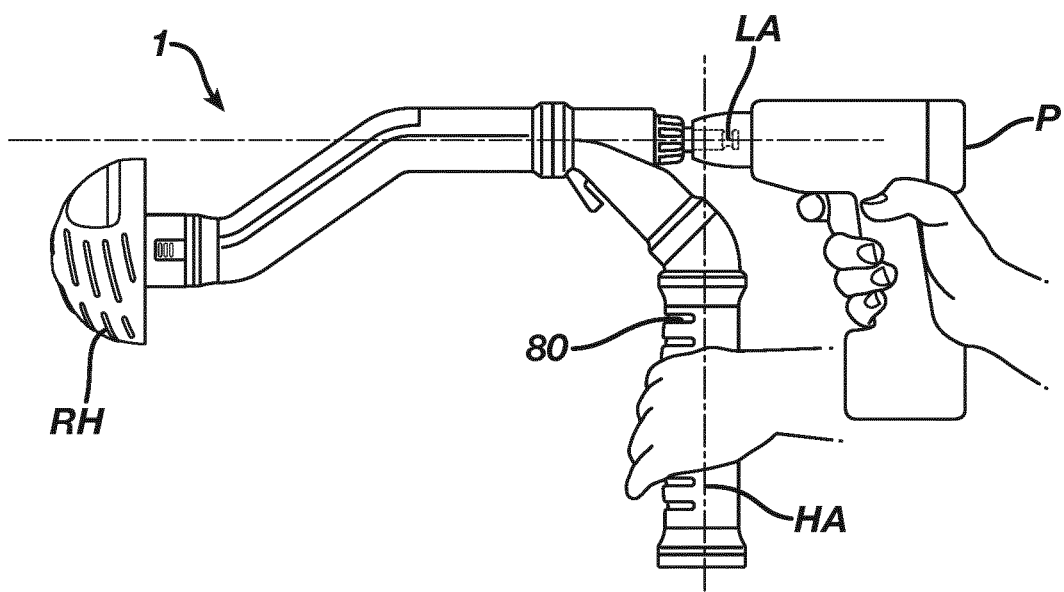
FIG. 4 shows a side view of the modular handle assembly depicting the "Reamer" configuration of FIG. 1.
Figure 5:
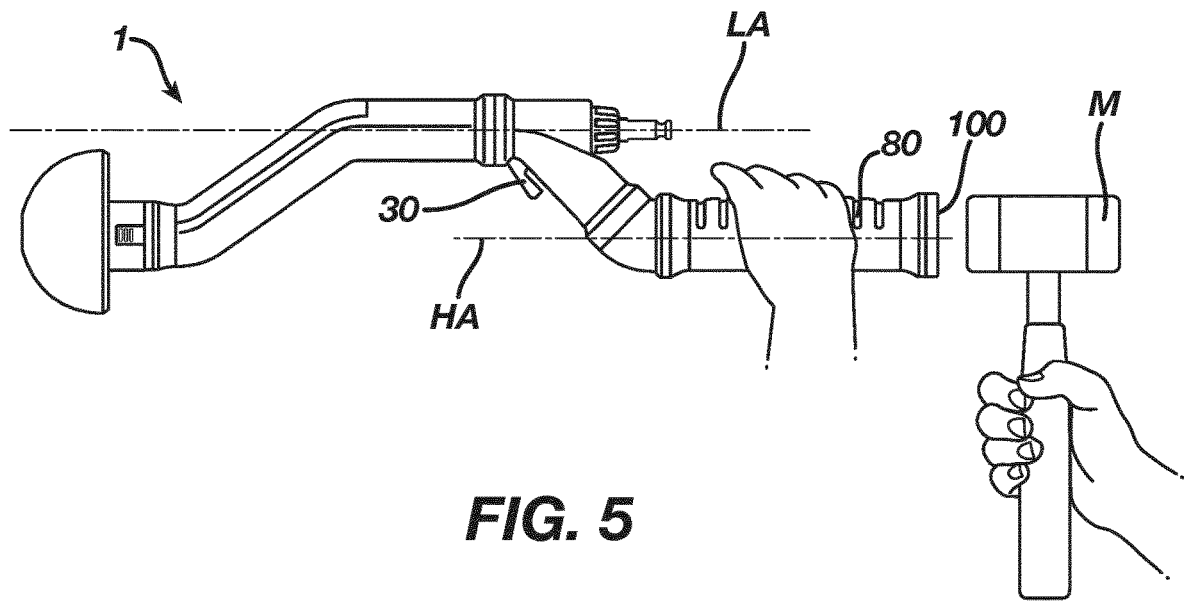
FIG. 5 shows a side view of the modular handle assembly depicting the "Impactor" configuration of FIG. 2.

As shown by FIGS. 4 and 5, the removable handle 80 enables the instrument 1 to be configured in at least a first and a second configuration. In the first configuration shown by FIG. 4, the handle 80 is configured so that the instrument 1 may be used as a reamer. In the second configuration shown by FIG. 5, the handle 80 is configured so that the instrument 1 may be used as an impactor.

The adjustable handle 80 is arrangeable relative to the body 10. In a first configuration, the handle is arranged such that the handle axis HA is in an offset alignment relative to the longitudinal axis LA. As show by FIG. 4, the handle is offset such that the handle axis HA is substantially perpendicular relative to the longitudinal axis LA. In the second configuration, the handle 80 is arranged such that the handle axis HA is in a parallel alignment relative to the longitudinal axis.

Figure 6:
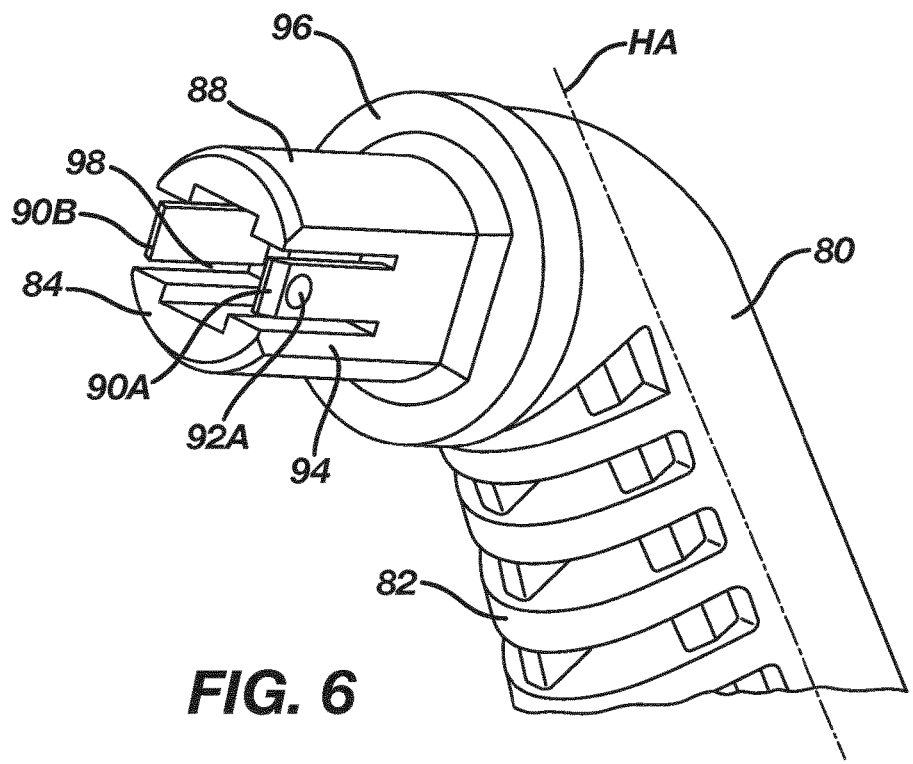
FIG. 6 shows a perspective view of the adjustable handle shown in FIG. 1 to FIG. 5.

Referring to FIG. 6, the first coupling member 88 is a portion of the handle 80 that extends from the grip 82 to the leading end 84 of the handle 80. The first coupling member 88 extends away from grip 82 at an angle offset relative to the handle axis HA. The first coupling member 88 extends away from grip 82 at an angle of 45 degrees relative to the handle axis HA angle of 45 degrees. Of course, as a person of skill would understand other offset angles are of course possible.

The first coupling member 88 has a sidewall 94 that extends like a neck from shoulders 96 located a transition point between the first coupling member 88 and the grip 82. The resilient elements 90A, 90B are located in the sidewall 94. The resilient elements 90A, 90B are defined by gaps in the sidewall 94 that extend from a midpoint of the sidewall 94 to the leading end 84.

The sidewall 94 surrounds a recess 98. The recess 98 is provided to allow the first coupling member 88, including the resilient elements 90A, 90B, to flex as it is being pressed into the second coupling member 20. For example, as the first coupling member 88 is being engaged with the second coupling member 20, the resilient element 90 deflects inwardly. Once the first coupling member 88 is seated correctly the protrusion 92 snap fits into in the aperture 22. The location of the protrusion 92 in the aperture 22 locks the handle 80 to the body 10.

The sidewall 94 defines the curved rectangular outer profile of the first coupling member 88. The curved rectangular outer profile has a first and a second flat surface on opposed side joined by opposed curved sides. Of course, as a person of skill would understand the sidewall 94 can define any suitably shaped outer profile of the first coupling member.

The internal sidewall 22B forming the cavity 22 of the second coupling member 20 has a shape that matches the shape of the external sidewall 94 of the second coupling member 88. In this way, when the coupling members 88, 20 are engaged they form a press-fit.

Figure 7:
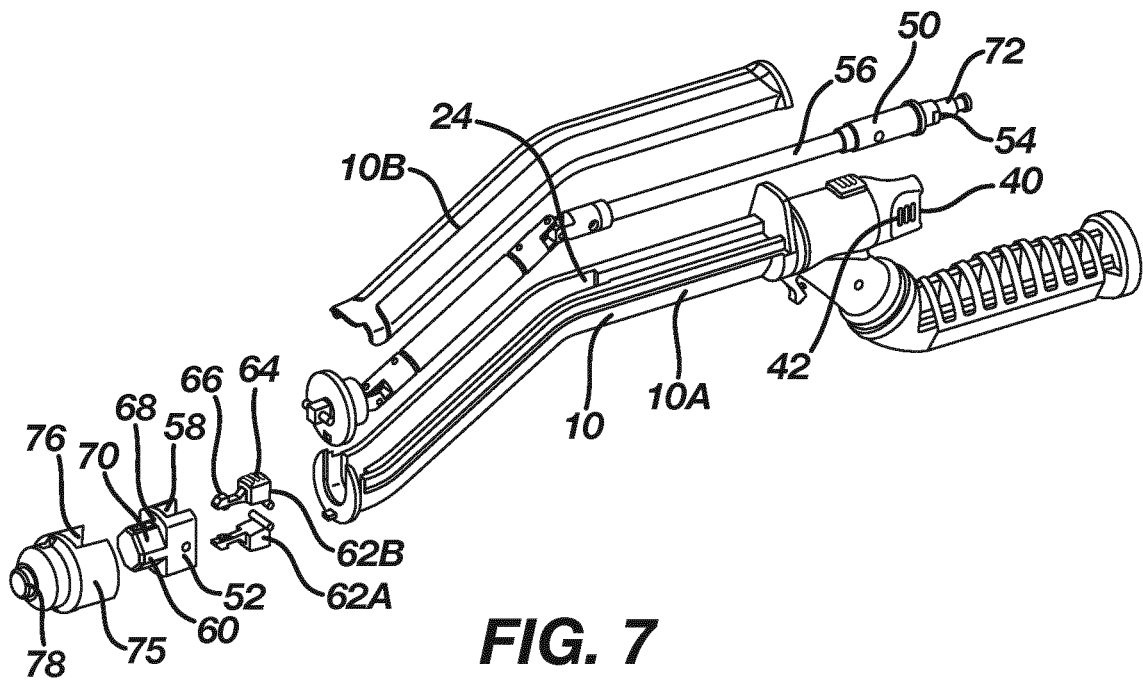
FIG. 7 shows an exploded perspective view of the modular handle assembly shown in FIG. 1 to FIG. 5.

Referring to FIG. 7, the instrument 1 has a drive 50. The drive 50 has a first connector 52 linked to a second connector 54 by a drive shaft 56. When the drive 50 is assembled into the instrument, the first connector 52 is located adjacent the distal end 14. The first connector 20 is adapted to be connected to a driven instrument, such as reamer head or an acetabular cup prosthesis. The second connector 54 is located adjacent the proximal end 16. The second connector 54 is adapted to be connected to a driving instrument, such as a power tool.

The body 10 has a first part 10A and a second part 10B. The first part 10A includes a channel 26 running from the distal end 14 to the proximal end 16. The second part 10B is connected to the first part 10B and covers the channel 26.

The drive shaft 56 is arranged in the channel 26. The drive shaft 56 is coupled to the first and second connectors 52, 54. The drive shaft 56 transmits a torque applied to the second connector 54 to the first connector 52 in order to rotate the first connector 52 about the longitudinal axis LA.

The first connector 52 is a reamer coupling. The first connector 52 is capable of coupling a reamer head to the instrument 1, such as the exemplary reamer head RH shown in FIG. 4. With the reamer head H coupled to the instrument 1, the instrument 1 may be used to perform a reaming procedure.

Continuing with reference to FIG. 7, the instrument 1 includes an adapter 75. The adapter 75 is couplable to the first connector 52 to adapt the instrument 1 to be coupled to an acetabular cup trial or acetabular cup prosthesis, such as the acetabular cup prosthesis shown in FIG. 5. The adapter has a first portion 76 configured to couple to the first connector 52 and a second portion 78 configured to couple to an acetabular trial or acetabular cup prosthesis P. With the trial or prosthesis P coupled to the instrument 1, the instrument 1 may be used to perform an impaction procedure.

The second region 78 is cylindrical in shape. The second region 78 has a thread for coupling the adapter 100 to the acetabular cup prosthesis.

FIG. 2 shows the adapter 75 arranged on the first connector 52. With the adapter 75 in position, the first connector 52 is configured to receive the acetabular cup prosthesis P.

Referring again to FIG. 7, the first connector 52 is a body defining a first portion 58 adapted to be coupled to the drive shaft 56 and a second portion 60 adapted to receive and be coupled to a reamer head RH.

The first connector 52 houses a set of sprung jaws 62A, 62B. The set of sprung jaws 62A, 62B are resiliently held in the first connector 52. The jaws 62A, 62B each include a button 64 and a tooth 66. The button 64 is arranged in the first portion 58 and the tooth 66 is arranged in the second portion 60. The tooth 66 is biased to be resiliently engaged with a coupling portion of the reamer head RH or a coupling portion 76 of the adapter 75. The button 64 is pressed to release the tooth from the coupling portion to enable the reamer head RH or adapter 75 to be removed from the first connector 52.

The exemplary coupling provided by the set of sprung jaws 62A, 62B can of course be varied and other mechanism to retain a reamer head RH or adapter 75 are of course possible and within the scope of the present invention.

The transition between the first portion 58 and the second portion 60 defines an abutment surface 68. The abutment surface 68 extends about the perimeter defining the second portion 60. The abutment surface 68 is arranged to abut a flat or planar base RB of the reamer head RH, such as a base RB shown in FIG. 8. In use, the abutment surface 68 abuts the reamer head RH to minimize movement the reamer head RH relative to the first connector 52. Restricting movement of the reamer head RH relative to the instrument 1 is beneficial to ensuring that the instrument 1 reams a cavity in a bone of a size expected by an operator of the instrument 1.

The second portion 60 is defined by a faceted surface 70. The faceted surface 70 matches the shape of the opening that forms a coupling RC of the reamer head RH. The coupling RC is substantially square shaped with cut corners giving it an overall octagonal shape. The faceted surface 70 is correspondingly substantially square shaped. Similarly, to the shape of the coupling RC the corners are cut giving it an overall octagonal shape. The matching of the faceted surface 36 to the coupling RC provides a fixed fit between the first connector 52 and the reamer head RH. The matching fixes the reamer head RH to the first connector 52 and enables a torque applied to the instrument 1 to be transferred to the reamer head RH.

The second connector 54 has a power tool coupling 72. The power tool coupling 70 features a conventional coupling. For example, the coupling 70 may be a so-called Hudson coupling. Other couplings are of course possible, such as the coupling shown and described in pending U.S. patent application No. 62/548,490 and U.S. patent application No. 62/592,478, which are hereby incorporated by reference in its entirety.

The instrument 1 includes a dial 40 is an annular component coupled to the second connecter 54 adjacent the body 10. The dial 40 is manually operated to rotate the drive shaft 56. The dial 56 has a plurality of grooves 42 positioned about its perimeter for increasing friction between the fingers of the operator and the dial 40.

In use, the dial 40 is used by an operator to rotate the first connector 52. The dial 40 may be rotated when the adapter 75 is coupled to the first connector 52. The second portion 78 of the adapter 75 has threads. The second portion 78 is engageable with a threaded aperture in an exemplary acetabular trial or prosthesis P. Rotation of the dial 40 may facilitate coupling of the threads of the second portion 78 with the threaded aperture (not shown) of an exemplary acetabular trial or prosthesis P. The result of the coupling is depicted in FIG. 5 that shows the instrument in the second configuration.

A manner of operating the instrument 1 will now be described.

The operator selects between the positions according to the type of process the instrument 1 is to be used to perform. FIG. 4 shows the instrument 1 with the handle in the first position. FIG. 5 shows the instrument 1 with the handle in the second position.

FIG. 4 show the instrument 1 arranged in the first, reaming configuration. In the reaming configuration, the instrument 1 is set up to be used as a reamer. A reamer head H may be coupled to the first connector 52 and a power tool P may be coupled to the second connector 54.

To set up the instrument 1 to be used as a reamer, if the handle 80 is not yet coupled to the instrument 1, it is simply engaged with the handle coupling 12 in the first position. If the handle is arranged in the second position, the release lever 30 is pressed to release the handle 80. The handle 80 is removed from the handle coupling 12, arranged so that the handle axis HA is perpendicular to the longitudinal axis LA and re-engaged with the handle coupling 12.

With the handle in the first position, the instrument is set up to be used in an impaction process.

In the reaming configuration, the handle 80 is arranged in the first position. In the first position the handle axis HA is offset relative to the longitudinal axis LA. As shown in the FIG. 4, the handle may be offset by 90° and be perpendicular relative to the longitudinal axis LA.

In the arrangement represented by FIG. 4, the instrument 1 is set up to be used in a reaming process.

In the reaming process, the handle 80 is gripped by an operator and the instrument 1 is used to press the reamer head RH against a bone, for example an acetabular cup, through manipulation of the power tool P. In the reaming process, the reamer head RH is used to ream a hemispherical cavity in a bone.

Figure 8:
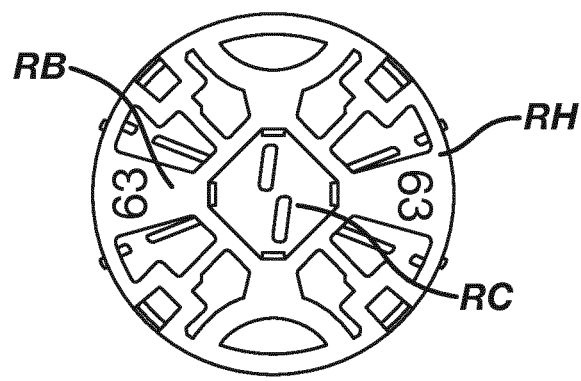
FIG. 8 shows a plan view of Grater that connects to modular handle during the "Reamer" configuration as shown in FIG. 4.

The operator may use a plurality of different sized reamer heads RH during the reaming process. An exemplary reamer head with a size "63" is shown in FIG. 8. The reamer heads RH of differing sizes are used to ream a cavity step-wise by incrementally increasing the diameter of the cavity until an appropriately sized cavity has been made.

To connect a reamer head RH to the instrument 1, the reamer head RH is pressed onto the first connector 52 to engage the teeth 66 of each jaw member 62A, 62B. To remove the in-situ reamer head RH buttons 64 are actuated to remove the teeth 66 from the in-situ reaming head RH. The in-situ reamer head may be removed by an operator or someone assisting the operator.

Referring to FIG. 5, the instrument 1 is arranged in a second configuration. In the second configuration, the handle 80 is arranged in the second position, and the adapter 75 is coupled to the first connector.

With the handle 80 in the second position and the adapter 75 connected to the first connector 52, the instrument 1 is arranged in an impaction configuration.

In the impaction configuration, an acetabular cup trial or prosthesis P may be coupled to the instrument 1 and impacted into a cavity in the bone formed during the reaming process.

To set up the instrument 1 for the impaction process, the handle 80 is arranged to be in the second position. If the handle 80 is not yet coupled to the instrument 1, it is simply engaged with the handle coupling 12 in the second position.

If the handle is arranged in the first position, the release lever 30 is pressed to release the handle 80. The handle 80 is removed from the handle coupling 12, arranged so that the handle axis HA is parallel to the longitudinal axis LA and re-engaged with the handle coupling 12. In this arrangement, the handle is in the second position and is set up to be used in an impaction process.

To couple an acetabular cup trial or prosthesis P, an operator selects an appropriate acetabular cup trial or prosthesis P. The operator arranges the acetabular cup trial or prosthesis P and rotates the dial 40. The threaded second portion 78 engages with a threaded aperture in the acetabular cup trial or prosthesis P to couple the instrument 1 to the acetabular cup trial or prosthesis P.

With the acetabular cup trial or prosthesis P coupled, the instrument 1 is set up to be used during an impaction process.

With the instrument 1 set up in an impaction configuration and an acetabular cup trial or prosthesis P coupled at the distal end 16, the operator grips the handle 80 with one hand and positions the instrument 1 relative to the bone in which the cavity has been formed during the reaming process.

Since the handle 80 is the second position, the impaction plate 100 is arranged in a position suitable for it to be struck by a surgical mallet M, or other suitable device. In the arrangement shown, the impaction plate 100 is arranged to be perpendicular relative to the longitudinal axis LA.

With one hand holding the instrument 1 in a desired position and orientation, the operator uses the other hand, to strike the impaction plate 100 with the surgical mallet M. The process of striking is repeated until the operator is satisfied that the acetabular cup trial or prosthesis P has been appropriately seated.

The operator may then actuate the dial 40 to decouple the instrument 1 from the acetabular cup trial or prosthesis P and removes the instrument 1 leaving the trial or prosthesis P in place.

To manufacture the instrument 1, the body 10, removable handle 80, dial 40 and jaw members 62A, 62B are fabricated by injection molding. These components 10, 80, 40, 62A and 62B are manufactured of a plastics material. Suitable plastics materials include polyacrylamide and MED Polyamide 12 (also known as Nylon 12).

The first connector 52, second connector 54, drive shaft 56 and adapter 75 are fabricated using injection molding. These components 52, 54, 56 and 75 are manufactured of a metal material. Suitable metal materials stainless steel. For example, type 17-4 PH stainless steel may be used Of course the instrument 1 can be made using other manufacturing techniques and fabricated from other materials as a person of ordinary skill would understand.

The components are assembled together in a conventional way to form the instrument 1.

FIGS. 9 to 13 show an instrument 2 of a second embodiment of the present invention. The instrument 2 is substantially the same as the instrument 1, with the exception of the handle coupling, the handle and the dial. In the second embodiment, the instrument 2 has a handle coupling 212, a handle 280 and a dial 240.

For simplicity the parts that differ between the instrument 1 and the instrument 2 will now be described. All other parts not described are identical to those of the instrument 1.

Figure 9:
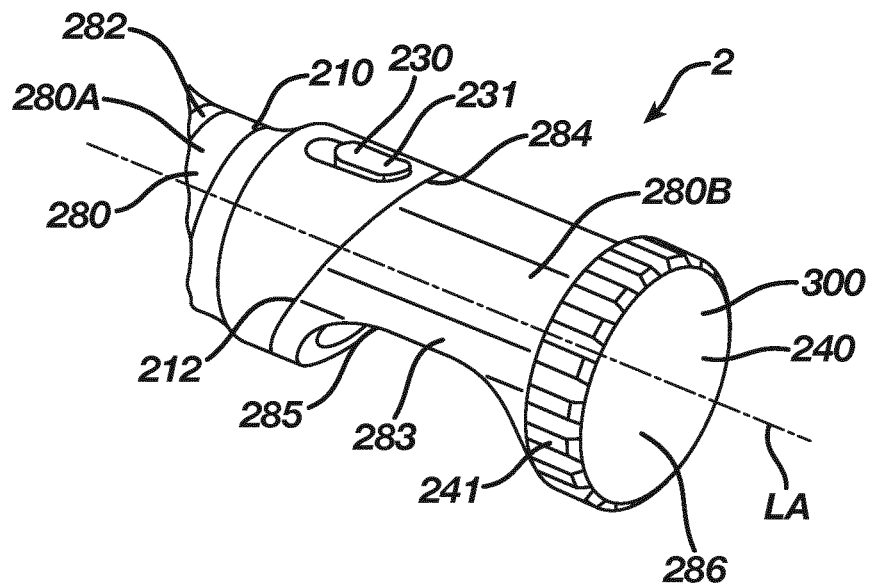
FIG. 9 shows an instrument 2 of a second embodiment of the present invention, depicting the "Impactor" configuration.

Referring to FIG. 9, the handle 280 forms part of the body 210. The handle has a fixed part 280A and a moveable part 280B. The moveable part 280B is rotatably coupled to the fixed part 280A by the handle coupling 212.

Figure 12:
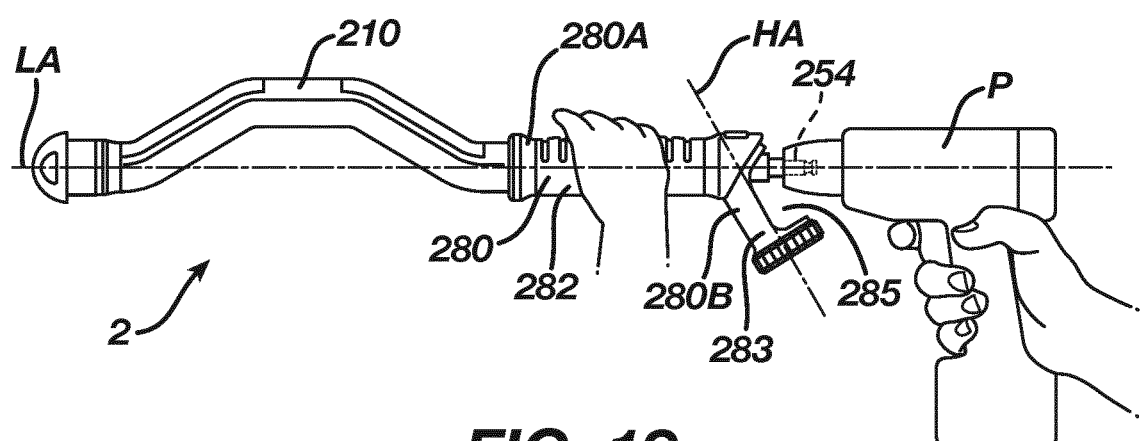
FIG. 12 shows a side view of the modular handle assembly depicting the "Reamer" configuration of FIG. 10.
Figure 13:
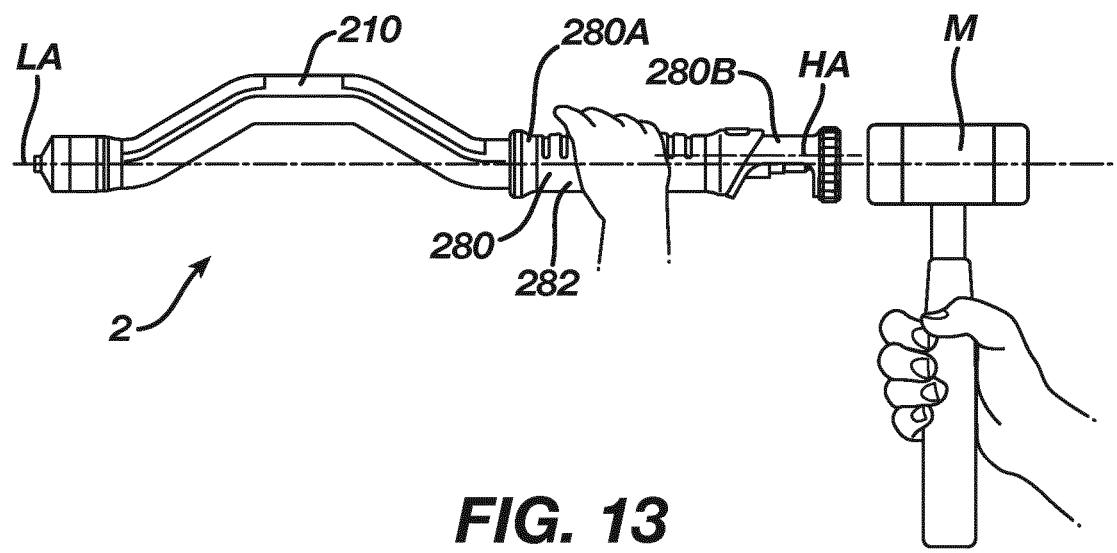
FIG. 13 shows a side view of the modular handle assembly depicting the "Impactor" configuration of FIG. 9.

The handle coupling 212 is configured to enable transitioning of the instrument 2 between the reaming and the impaction configurations shown by FIGS. 12 and 13, respectively.

As can be seen by FIGS. 12 and 13, the fixed part 280A is part of a body 210 of the instrument 2. The fixed part 280A is aligned with a longitudinal axis LA of the body 210. The fixed part 280A defines a grip 282.

Figure 11:
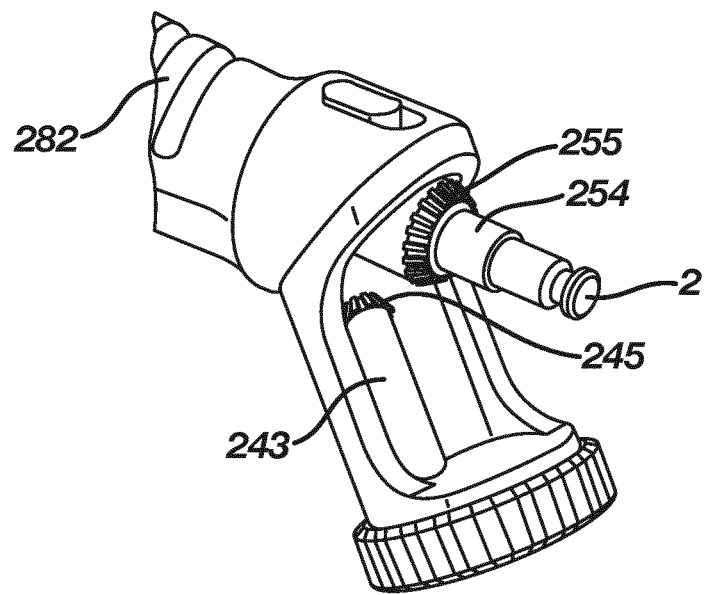
FIG. 11 shows an instrument 2 of a second embodiment of the present invention, a perspective view of the adjustable housing shown, depicting the "Reamer" configuration.

Referring again to FIG. 9, the moveable part 280B of the handle 280 has a leading end 284 spaced apart from a trailing end 286 along a handle axis HA by a housing 283. The housing 283 is for housing a second connector 254 of a drive 250 of the instrument 2, as shown in FIG. 11, when the instrument 2 is in the impaction configuration as shown by FIGS. 9 and 13.

Referring again to FIG. 9, the moveable part 280B has a window 285 in the housing 283 through which the second connector 254 passes as the moveable part 280B is transitioned between the reamer and impaction configurations.

A leading end 284 is coupled rotatably to the fixed part 280A by the handle coupling 212. The handle coupling 212 is a swivel joint 396.

The handle coupling 212 has a locking arrangement 230. Simliarlly to the release lever 30, the locking arrangement 230 locks the adjustable part, for example the moveable part 280B, of the handle 280 in one of the first and second positions and a release switch 231 releases the lock to allow the adjustable part to be rearranged.

In a first handle position, as shown by FIG. 12, the movable part 280B is arranged such that the handle axis HA is offset relative to the longitudinal axis LA of the instrument 2. With the handle in the first position, the second connector 254 is arranged through the window 285 and is accessible for engagement by a power tool P.

In a second handle position, as shown by FIG. 13, the movable part 280B is arranged such that the handle axis HA is aligned with the longitudinal axis LA. With the handle 280 in the second position, the second connector 254 is located in the housing 385.

Referring back to FIG. 9, in the instrument 2 a dial 240 similar to the dial 40 of the reamer 1 is located in the trailing end 286 of the handle 280.

The dial 240 has a knob 241, which defines an impaction plate 300 of the handle 280. The dial 240 is rotatable about the handle axis HA through manipulation of the knob 241. Rotation of the knob 241 causes the dial 240 to rotate to enable an acetabular cup trial or prosthesis P to be coupled to the instrument 2.

Referring to FIG. 11, the dial 240 has a protrusion 243. The protrusion 243 has a beveled end 245. The protrusion 243 is located in the housing 283. The protrusion 243 extends from the knob 241 relative to the handle axis HA.

In the impaction configuration, as shown by FIG. 13, the beveled end 245 engages with a beveled portion 255 of the second connector 254.

Figure 10:
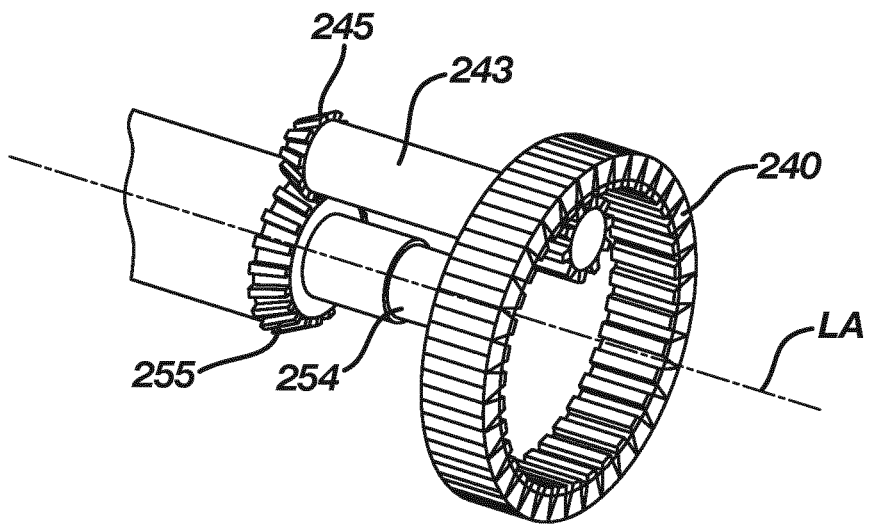
FIG. 10 shows the sun gear arrangement under the housing assembly at the proximal end during "Impactor" configuration shown in FIG. 9.

With reference to FIG. 10, the dial 240 has a sun gear arrangement coupling the knob 241 (not shown in FIG. 10 for simplicity) to the protrusion 243 and the beveled portion 255. Due to the sun gear arrangement, a torque applied to the knob 241 by an operator is transferred to the second connector 254. The transferring of the torque enables, for example, an acetabular cup prosthesis P to be coupled to the instrument 2.

Similarly to the use of instrument 1, the instrument 2 is arranged in the reaming and impaction configurations and is usable as either a reamer or an impactor. The instrument 2 is arranged in one of the configurations by orienting the handle 280 in one of the first and second positions through releasing the locking arrangement 230 and moving the handle into one of the positions as shown by FIGS. 11 and 12.

The instrument 2 is used in the same was as described for the instrument 1.

To manufacture the instrument 2, the body 210, the fixed part of the handle 280A, and jaw members 262A, 262B are fabricated by injection molding. These components 210, 280A, 262A and 262B are manufactured of a plastics material. Suitable plastics materials include polyacrylamide and MED Polyamide 12 (also known as Nylon 12).

The components of dial 240, the first connector 252, second connector 254, drive shaft 256, adapter 275 and the movable part of the handle 280B are fabricated using injection molding. These components 240, 252, 254, 256, 275 and 280B are manufactured of a metal material. Suitable metal materials stainless steel. For example, type 17-4 PH stainless steel may be used Of course the instrument 1 can be made using other manufacturing techniques and fabricated from other materials as a person of ordinary skill would understand.

Figure 14:
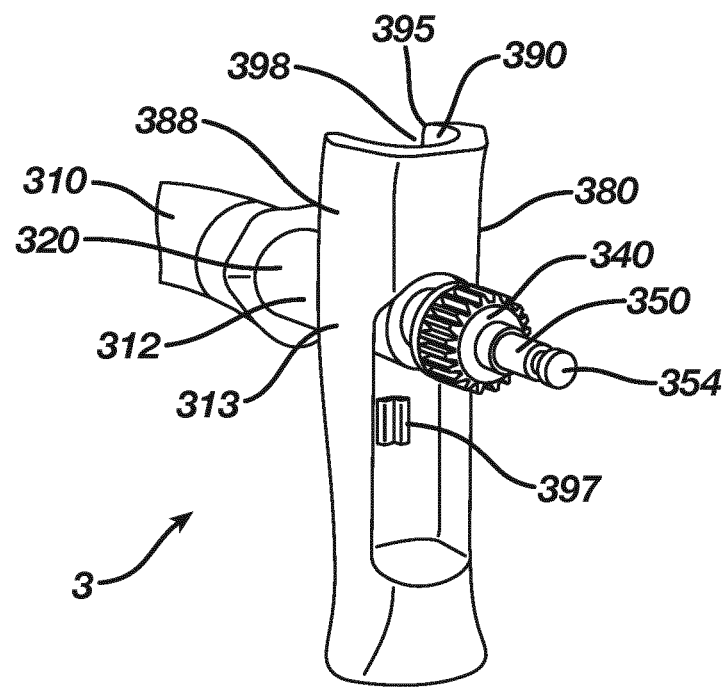
FIG. 14 shows an instrument 3 of a third embodiment of the present invention, depicting the "Reamer" configuration.
Figure 15:
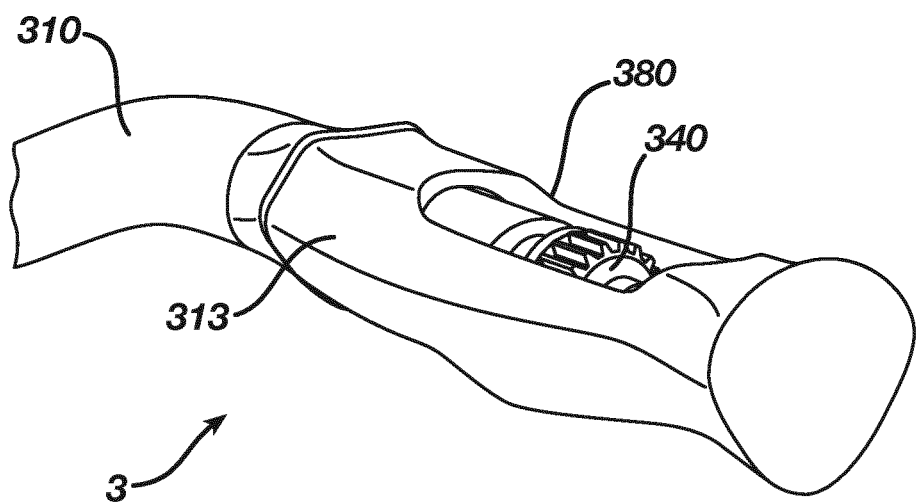
FIG. 15 shows an instrument 3 of a third embodiment of the present invention, depicting the "Impactor" configuration.

FIGS. 14 and 15 show an instrument 3 of a third embodiment of the present invention. The instrument 3 is substantially the same as the instrument 2, with the exception that of the handle coupling and the handle.

For simplicity the parts that differ between the instrument 2 and the instrument 3 will now be described. All other parts not described are identical to those described for the instrument 1 and 2.

Similarly, to the instrument 2, an adjustable handle 380 of the instrument 3 is coupled to part of a body 310. In contrast, where the moveable part 280B of the handle 280 may be swiveled between the first and second positions, the handle 380 is pivotable relative to the body 310.

A handle coupling 312 enables the handle 380 to be arranged between the first and second positions to configure the instrument 3 to be used as either a reamer or an impactor.

The handle coupling 312 includes a pivot pin 313. The pivot pin 313 pivotably couples the handle 380 to the body 310.

The handle is arrangeable between a first position shown in FIG. 13 and a second position shown in FIG. 14. With the handle in the first position, the instrument 1 may be used for reaming. With the handle in the second position, the instrument 1 may be used for impacting.

In the first position, the handle 380 is moveable about the pivot pin 313.

In the second position, the handle is locked to the body 310 by coupling members 320, 388 of the handle coupling 312. The first coupling member 388 is located on the handle 380 and a second coupling member 320 is provided by the body 320. The first coupling member 388 snap-fits over the second coupling member 320 to lock the handle 380 in position relative to the body 310

The first coupling member 388 is defined by a resilient jaw 390 in the handle 380. The jaw 390 has a cylindrical shaped inner cavity 398 and a mouth 395 that leads into the cavity 398.

The second coupling member 320 is a portion of the body 310. The portion of the body 310 has a cylindrical outer profile, which a diameter that matches the cylindrical inner profile defining the cavity 398.

Due to the resilience of the jaw 390 as the first coupling member 388 is pivotally engaged with the second coupling member 320 the mouth 395 widens. The widening of the mouth continues until a point is reached when jaw resiliently snaps over the second coupling member 320.

A dial 340 of the instrument 3 is located adjacent a second connector 354 of the drive 350. Similarly to the instruments 1 and 2, the dial 340 is used to rotate a first connector when an acetabular trial or prosthesis is being coupled to the instrument 3. The instrument 3 has a stop 397. The stop 485A arranged to engage with a groove 474 of the dial 472 to stop the dial 472 from rotating when the instrument 3 is arranged to be used as an impactor.

Similarly to the use of instruments 1 and 2, the instrument 3 is arranged in the reaming and impaction configurations and is usable as either a reamer or an impactor. The instrument 3 is arranged in one of the configurations by orienting the handle 380 in one of the first and second positions through releasing the handle coupling 312 and moving the handle 380 into one of the positions as shown by FIGS. 13 and 14.

The instrument 3 is used in reaming process as described for the instrument 1. The instrument 3 is used in the impaction process substantially as described for the instrument 1, with the exception of the coupling of the acetabular cup trial or prosthesis P to the first connector. Since the dial 340 is prevented from rotating in the second position due to the stop 385A, the adapter 75 is connected and the acetabular cup trial or prosthesis P is coupled to the first connector whilst the handle 380 is still in the first position.

The exemplary embodiment 1, 2 and 3 of surgical instruments of the present invention are arrangeable between a plurality of configurations. In the first configuration, the instrument can be used as a reamer. In the second configuration, the instrument can be used as an impactor. Due to the manner in which the instrument can be switched between the configurations, the instruments are convenient and efficient in terms of reducing overall kit size for instruments used in a surgical procedure and in terms of surgical efficiency since the instrument is easy to use when compared to the prior art, which features a plurality of parts require disassembly during a reconfiguration process.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

Although preferred embodiments of the present invention have been shown and described, it will be appreciated by those skilled in the art that changes may be made without departing from the scope of the invention as defined in the claims.

In this specification, the terms "comprise", "comprises", "comprising" or similar terms are intended to mean a non-exclusive inclusion, such that a system, method or apparatus that comprises a list of elements does not include those elements solely, but may well include other elements not listed.

The reference to any prior art in this specification is not, and should not be taken as, an acknowledgement or any form of suggestion that the prior art forms part of the common general knowledge.

It will of course be understood that this description is by way of example only; alterations and modifications may be made to the described embodiment without departing from the scope of the invention as defined in the claims.

The invention claimed is:

1. An instrument comprising
a body comprising a distal end spaced apart from a proximal end relative to a longitudinal axis and a handle coupling located near the proximal end, the body defining a channel running between the distal end to the proximal end;
a drive comprising a first connector located adjacent the distal end and adapted to be connected to a driven instrument, a second connector located adjacent the proximal end and adapted to be connected to a driving instrument, and a drive shaft arranged in the channel, the drive shaft coupling the second connector to the first connector; and
an adjustable handle located near the distal end, the adjustable handle comprising a grip spacing apart a leading end from a trailing end along a handle axis, the leading end coupling the handle to the handle coupling, the trailing end shaped to define an impaction plate;
wherein (i) the adjustable handle is arrangeable relative to the body in a first and a second position, (ii) in the first position (a) the leading end is arranged relative to the handle coupling such that the handle axis is offset relative to the longitudinal axis, (b) the second connector is engageable by the driving instrument, and (c) the adjustable handle can be gripped by a user to provide additional support, and (iii) in the second position the leading end is arranged relative to the handle coupling such that the handle axis is parallel to the longitudinal axis.

2. The instrument of claim 1, wherein, in the second position, the impaction plate is perpendicular to the longitudinal axis.

3. The instrument of claim 1, wherein the adjustable handle is rotatably coupled to the handle coupling distal end of the body.

4. The instrument of claim 1, wherein the adjustable handle is removable from the handle coupling to enable arrangement of the adjustable handle in one of the first or second positions.

5. The instrument of claim 4, wherein the handle coupling comprises a faceted recess and the leading end of the adjustable handle is faceted; and
wherein the leading end of the adjustable handle is removable from the faceted recess and, due to the facets, is capable of being selectively arranged into the faceted recess in either the first or the second position.

6. The instrument of claim 5, wherein, in cross section, the faceted recess and the faceted leading end have the same polygonal shape.

7. The instrument of claim 1, further comprising a holding mechanism to hold the handle in the first and second positions.

8. The instrument of claim 7, wherein the holding mechanism comprises a latch to retain the handle in one of the first or second positions and a release mechanism to unlatch the latch so that the handle can be moved between the first and second positions.

9. An instrument comprising:
- a body having a proximal end and a distal end, the body defining a channel running from an opening in the proximal end to an opening in the distal end;
- a drive mechanism having a first coupling located near the proximal end connected by a drive shaft located in the channel to a second coupling located near the distal end, the drive shaft arranged to transmit torque applied to one of the couplings to the other;
- an actuator arrangeable between a first and a second position relative to the first coupling, wherein in the first position the actuator is engaged with the first coupling and is manipulatable to transmit an applied torque to the first coupling, and in the second position the actuator is disengaged from the first coupling and is unable to transmit a torque to the first coupling; and
- a holding mechanism to hold the actuator in the first and second positions, the holding mechanism comprises a latch to retain the actuator in one of the first or second positions.

\* \* \* \* \*